(12) United States Patent
Alba

(10) Patent No.: US 7,513,168 B2
(45) Date of Patent: Apr. 7, 2009

(54) JACK BOLT ACTIVATED TENSILE STRENGTH TEST MACHINE

(76) Inventor: Tony J. Alba, 1236 E. Michelle Ave., West Covina, CA (US) 91790

( * ) Notice: Subject to any disclaimer, the term of this patent is extended or adjusted under 35 U.S.C. 154(b) by 185 days.

(21) Appl. No.: 11/691,843

(22) Filed: Mar. 27, 2007

(65) Prior Publication Data

US 2007/0227259 A1 Oct. 4, 2007

Related U.S. Application Data

(60) Provisional application No. 60/786,892, filed on Mar. 29, 2006.

(51) Int. Cl.
*G01N 3/08* (2006.01)
(52) U.S. Cl. .......................... 73/826; 73/818
(58) Field of Classification Search ................... 73/856, 73/818, 826
See application file for complete search history.

(56) References Cited

U.S. PATENT DOCUMENTS

| | | | |
|---|---|---|---|
| 4,478,086 A * | 10/1984 | Gram .......................... 73/826 |
| 4,869,112 A * | 9/1989 | Gram et al. .................... 73/856 |
| 5,083,889 A | 1/1992 | Steinbock | |
| 5,405,210 A | 4/1995 | Tsui | |
| 5,948,994 A * | 9/1999 | Jen et al. ...................... 73/856 |
| 6,199,925 B1 | 3/2001 | Alba | |
| 6,267,422 B1 | 7/2001 | Alba | |
| 6,526,837 B1 * | 3/2003 | Grote et al. ................... 73/856 |
| 7,404,334 B2 * | 7/2008 | Saari et al. .................... 73/856 |

* cited by examiner

*Primary Examiner*—Harshad Patel
*Assistant Examiner*—Jonathan Dunlap
(74) *Attorney, Agent, or Firm*—Bruce A. Jagger

(57) ABSTRACT

A tensile strength testing machine comprises a frame assembly that defines a test zone. The frame assembly includes a frame member that has first and second opposed ends. The ends have inner sides that generally face one another across the test zone, and outer sides that are generally opposed to one another and the test zone. An arbor element is mounted for generally axial movement relative to the first end. The arbor element is slidably mounted in the first end. The arbor element projects inwardly into the test zone and outwardly from the outer side of the first end. The arbor element is adapted to being attached to a test specimen, which mounted in the test zone. A portion of the arbor element that projects outwardly from the outer side of the first end is generally surrounded by an array of jack bolts. The jack bolts are threadably mounted in a collar member that is substantially axially fixed relative to the arbor element. The jack bolts are positioned to bear generally against the outer side of the first end. Typically, at least a thrust collar, and, preferably, a load determining assembly are interposed between this outer side and the bearing ends of the jack bolts. Torquing down the jack bolts against the outer side of the first end places the arbor element in tension. This tensile load is applied to a test specimen mounted in the test zone, and the magnitude of the load is determined.

12 Claims, 2 Drawing Sheets

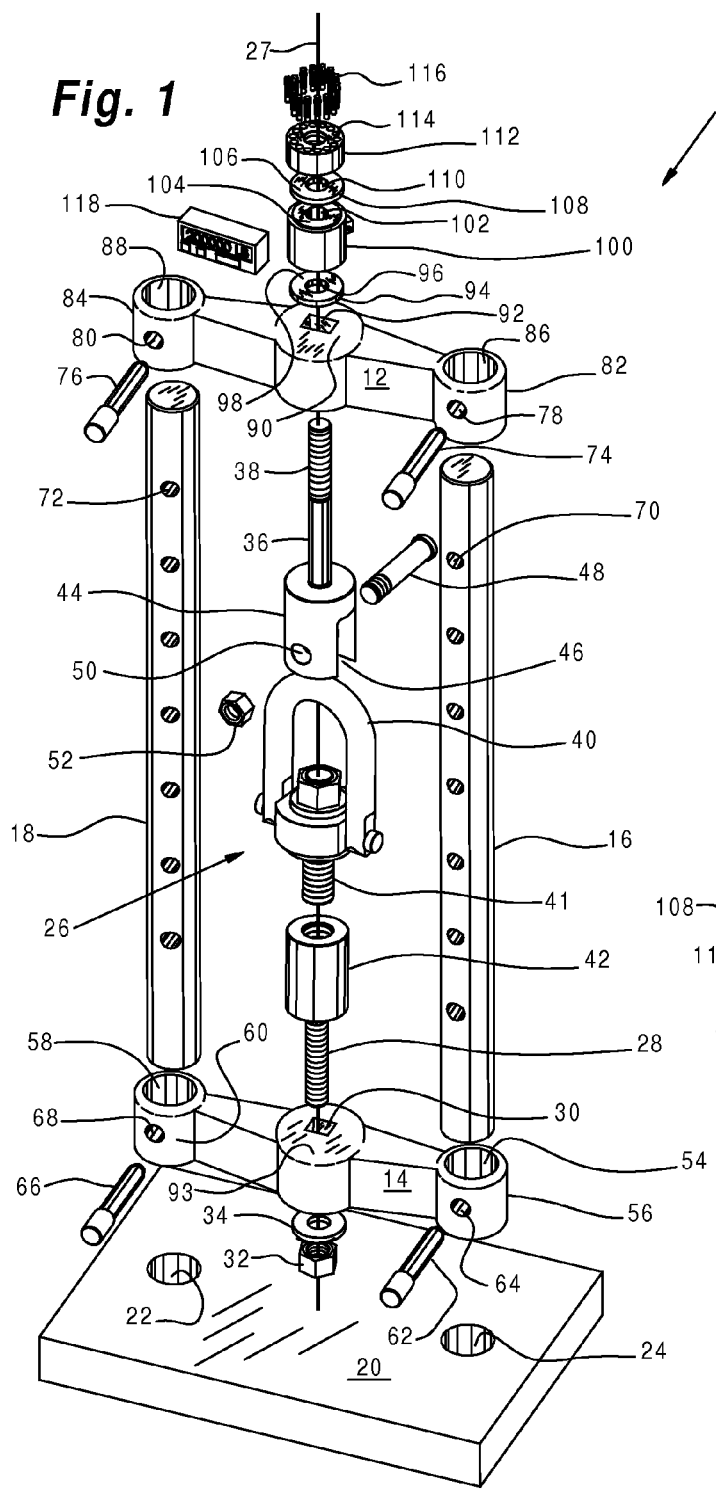
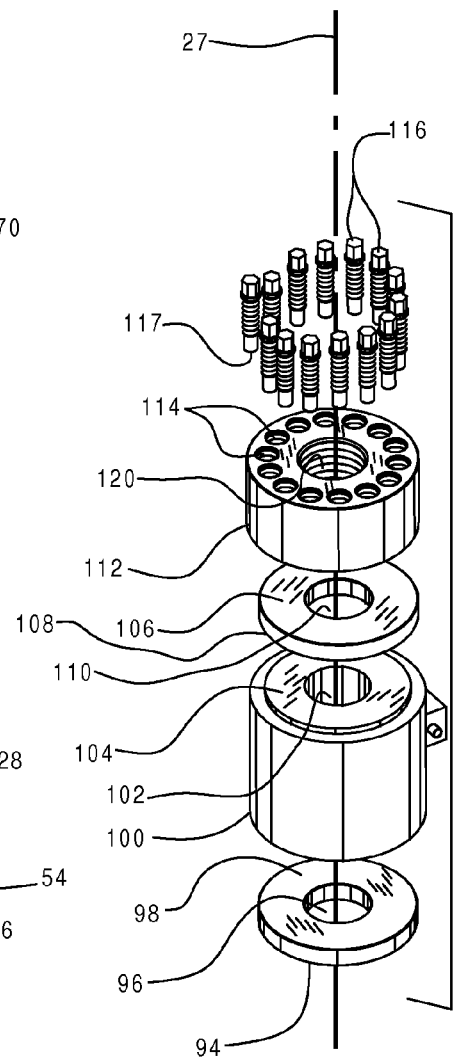
Fig. 1
Fig. 2

JACK BOLT ACTIVATED TENSILE STRENGTH TEST MACHINE

RELATED APPLICATIONS

This application claims the benefit of U.S. Provisional patent application Ser. No. 60/786,892, filed Mar. 29, 2006

BACKGROUND OF THE INVENTION

1. Field of the Invention

The invention relates in general to methods and devices for mechanically testing the tensile strength of an article, and, more particularly, embodiments of the present invention relate to jack bolt activated tensile strength testing machines.

2. Description of the Prior Art

Tensile strength testing machines and methods have been widely used for many years for determining the mechanical tensile strengths of various articles. The prior art devices and methods are not without their shortcomings. A major shortcoming of typical prior art devices and methods is that they are expensive to purchase and rely, for example, on hydraulic activators, or the like, which require maintenance, repair, and some skill in their operation. They are generally not quick enough or simple enough to use for purposes of proof testing manufactured articles in a manufacturing operation for purposes of quality control.

Some articles of manufacture are of such a critical nature that every one or at least a large percentage of those made must be tested individually to determine whether they meet predetermined strength requirements. This is generally referred to as proof testing. Such testing must be done on a continuous basis as a part of a manufacturing operation. It must be done quickly and easily, and the testing equipment must be reliable, rugged, and simple to operate. The costs of purchasing, maintaining and operating such proof testing equipment must be low. Previously proposed expedients tended to be unsuitable for use in a manufacturing environment, among other reasons, because of costs, complexity, maintenance cost, or slow cycle times.

Many devices had been proposed for the purposes of measuring and indicating mechanical strain. The indicating elements typically included, for example, visible read outs or printouts, data loggers, or the like. The measuring devices typically included compression and tension load cells and strain gauges of various types.

The use of jack bolts in a collar that surrounds and is in an axially fixed position relative to a bolt for purposes of imposing large loads on the shank of the bolt is known. See, for example, Alba U.S. Pat. No. 6,199,925, and Steinbock U.S. Pat. No. 5,083,889. Torquing down the jack bolts one by one permits the quick and simple imposition of very substantial loads on the shank of the bolt.

Swiveling hoist rings are widely used for safely lifting heavy loads in many different industries. Various swiveling hoist rings are shown, for example, in Tsui U.S. Pat. No. 5,405,210, and Alba U.S. Pat. No. 6,267,422. Because they are critical safety devices, swiveling hoist rings must be proof tested by their manufacturer. Proof testing generally involves placing the hoist rings in tension with a load that equals twice the rated capacity of the hoist ring. Thus, a hoist ring that is, for example, rated at a lifting capacity of 20,000 pounds is designed to have an ultimate strength of 100,000 pounds, and must (by government regulation) be proof tested to double its rated load, or 40,000 pounds. The test loads are imposed in tension. At least during the design phase of a new hoist ring, and following changes in an existing hoist ring product, it is tested to failure. If a test specimen of a hoist ring design fails at 80,000 pounds, it would not be rated at more then 16,000 pounds load capacity. The test equipment that is used for these tests must be certified as to accuracy. Reliable, certifiable, convenient, and inexpensive testing equipment is required to perform such tests.

These and other difficulties of the prior art have been overcome according to the present invention.

BRIEF SUMMARY OF THE INVENTION

The present invention has been developed in response to the current state of the art, and in particular, in response to these and other problems and needs that have not been fully or completely solved by currently available tensile strength testing machines and methods. Thus, it is an overall object of the present invention to effectively resolve at least the problems and shortcomings identified herein. In particular, it is an object of the present invention to provide a tensile testing machine wherein the load which is generated for the purpose of tensioning the test specimen is applied through the use of hand operated wrenches applied to jack bolts that are arrayed in a collar element generally around an arbor element. It is also an object of the present invention to provide a tensile strength testing machine that is particularly adapted to proof testing manufactured articles. Finally, it is an object of the present invention to provide a tensile strength testing machine that is particularly adapted to quickly, easily, and reliably proof testing manufactured articles in a manufacturing operation for purposes of quality control.

According to a preferred embodiment, a tensile load is imposed on a test specimen by using a frame assembly that defines a test zone and includes a frame member that has a side generally opposed to the test zone. An arbor element is mounted for generally axial movement relative to the side so that the arbor element projects inwardly into said test zone and outwardly from the side of the frame member. The test specimen is mounted in test zone. This mounting includes attaching the test specimen to the arbor element. An array of jack bolts surrounds a portion of the arbor element that projects outwardly from the side. The arbor elements are threadably mounted in a collar member that is axially fixed relative to said arbor element. That is, during a test the collar member does not move relative to the arbor element. The arbor element is generally free to move axially relative to the side. The tensile load is applied to the specimen by tightening the jack bolts generally against the side. Typically, at least a thrust washer element is positioned between the bearing ends of the jack bolts and the side for purposes of distributing the load equally around the arbor element. Other elements or members such as, for example, a load cell can be positioned around the arbor element between the bearing ends of the jack bolts and the side, if desired.

To acquaint persons skilled in the pertinent arts most closely related to the present invention, a preferred embodiment of a mechanical tensile strength testing machine that illustrates a best mode now contemplated for putting the invention into practice is described herein by, and with reference to, the annexed drawings that form a part of the specification. The exemplary machine is described in detail without attempting to show all of the various forms and modifications in which the invention might be embodied. As such, the embodiments shown and described herein are illustrative, and as will become apparent to those skilled in the arts, can be modified in numerous ways within the scope and spirit of the invention, the invention being measured by the appended claims and not by the details of the specification or drawings.

Other objects, advantages, and novel features of the present invention will become more fully apparent from the following detailed description of the invention when considered in conjunction with the accompanying drawings, or may be learned by the practice of the invention as set forth herein.

BRIEF DESCRIPTION OF THE DRAWINGS

The present invention provides its benefits across a broad spectrum of tensile strength testing machines. While the description which follows hereinafter is meant to be representative of a number of such applications, it is not exhaustive. As those skilled in the art will recognize, the basic apparatus taught herein can be readily adapted to many uses. This specification and the claims appended hereto should be accorded a breadth in keeping with the scope and spirit of the invention being disclosed despite what might appear to be limiting language imposed by the requirements of referring to the specific examples disclosed.

Referring particularly to the drawings for the purposes of illustrating the invention and its presently understood best mode only and not limitation:

FIG. 1 is an exploded perspective view of a preferred embodiment of the tensile strength testing machine invention with a swiveling hoist ring test specimen mounted therein.

FIG. 2 is an exploded perspective view of the arbor assembly, without the arbor element, of the embodiment of FIG. 1.

DETAILED DESCRIPTION OF THE PREFERRED EMBODIMENTS

Figure 3:
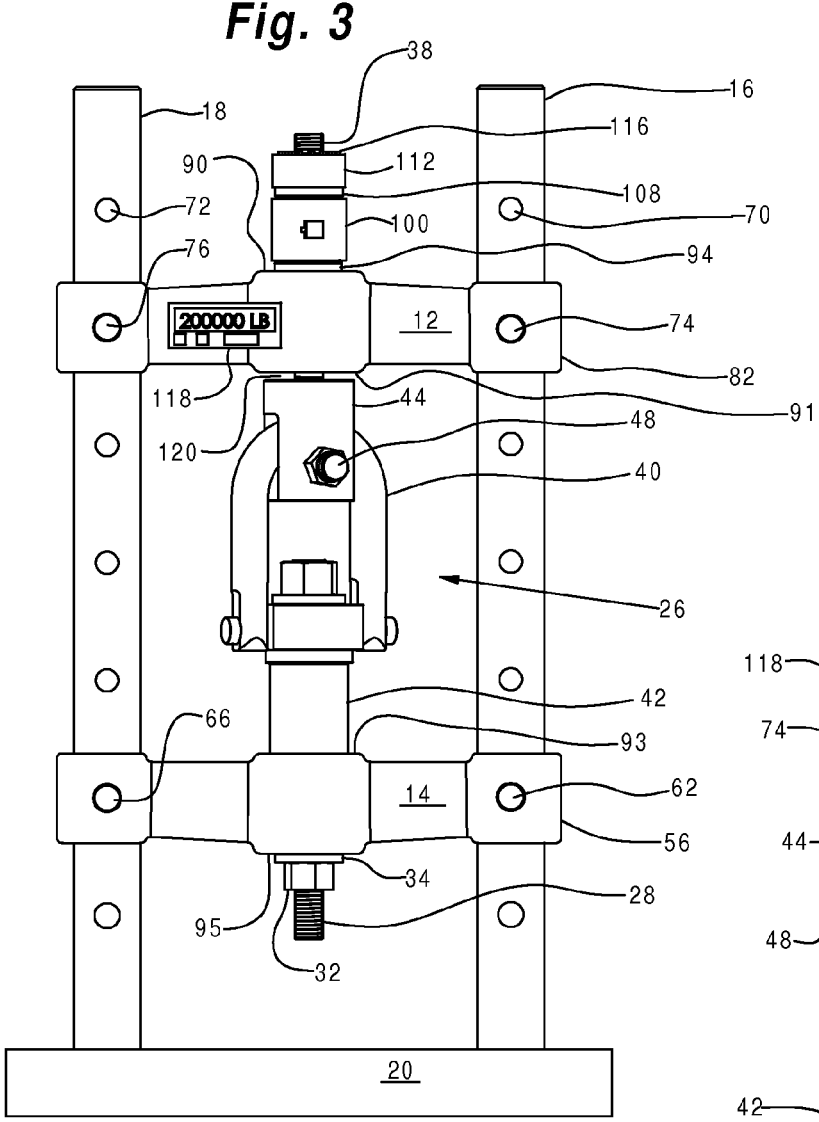
FIG. 3 is a front view of the tensile strength testing machine of FIG. 1.
Figure 4:
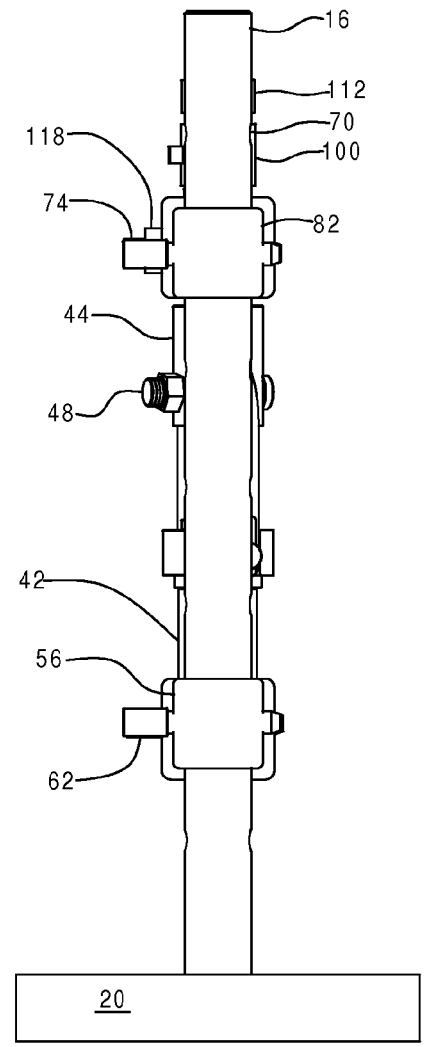
FIG. 4 is a side view of the tensile strength testing machine of FIG. 1.

Referring now to the drawings wherein like reference numerals designate identical or corresponding parts throughout the several views. It is to be understood that the drawings are diagrammatic and schematic representations of various embodiments of the invention, and are not to be construed as limiting the invention in any way. The use of words and phrases herein with reference to specific embodiments is not intended to limit the meanings of such words and phrases to those specific embodiments. Words and phrases herein are intended to have their ordinary meanings, unless a specific definition is set forth at length herein.

Referring particularly to the drawings there is illustrated generally at 10, a tensile strength testing machine for imposing a tensile load on a test specimen mounted in a test zone indicated generally at 26. In the embodiment chosen for purposes of illustration, the illustrated test specimen is a swiveling hoist ring that includes a lifting loop 40 and a mounting stud 41 mounted in a tensile strength testing configuration in test zone 26.

A frame assembly surrounds the test zone 26. The frame assembly generally includes generally opposed first and second ends, for example, crosshead element 12 and footing element 14, each of which has an inner side and an outer side. The inner sides, for example, 91 and 93, generally face one another across the test zone 26, and the outer sides, for example, 90 and 93, are generally opposed to one another. The respective ends are maintained in a spaced apart relationship in the frame assembly. The frame assembly has an axis 27 extending generally between the opposed ends through the test zone, and the test load is preferably applied to the test specimen generally along this axis. The mounting, load imposing, and load measuring mechanisms are usually arrayed along this axis.

The frame assembly serves to mount an arbor assembly by means of which a test load is generated and applied to the test specimen. In the embodiment chosen for illustration, an arbor element extends slidably through the first end at passage 92 from the outer side 90 into or at least towards the test zone 27. The arbor element includes, for example, threaded portion 38 and shank portion 36. In the embodiment chosen for illustration, a collar member in the form of load imposing flange element 112 is mounted to the arbor element on the outer side of the first end. In the illustrated embodiment the flange element 112 is provided with a threaded central bore 120. Flange element 112 is typically in the form of a collar that surrounds a portion of the arbor element that extends from a side of a frame member that is opposed to the test zone 26. Central bore 120 is adapted to threadably receiving threaded portion 38 of the arbor element. This threaded engagement allows the position of flange element 112 relative to the threaded portion 38 to be adjusted during assembly, but retains the flange element in a fixed location relative to the threaded portion 38 while a test is being conducted.

Passage 92 is slightly large than the arbor element to permit it to slide axially and move slightly laterally. The arbor element can shift slightly laterally to align itself with axis 27 as a test load is applied. Likewise, passage 30 in the second end is slightly larger than threaded mounting shaft 28 to permit slight lateral shifting of the mounting fixture assembly for alignment purposes. The arbor element and the threaded mounting shaft 28 are preferably aligned with one another along axis 27 so that a load applied to the test specimen does not exert a bending force on the arbor element or mounting shaft. The configuration of the test specimen may be such that a bending force is applied to some or all of the specimen itself.

The engagement between the arbor element and the load imposing flange element 112 is provided in the illustrated embodiment by way of mating threads, but, as will be understood by those skilled in the art, other engagement arrangements may be provided, if desired. The flange element 112 may, for example, be permanently mounted or removably pinned, or the like, to the arbor element. The flange element 112 should be mounted to the arbor element in a position that is axially fixed while a test is being conducted. That is, while a test is being conducted the flange element and the arbor element should not move relative to one another. Depending on the intended purpose of a particular embodiment of the test machine, the location of the flange element 112 or other collar member relative to the arbor element may or may not be adjustable.

A plurality of threaded bores, of which 114 is typical, extend generally axially through the collar member. The threaded bores extend generally parallel to and spaced laterally from axis 27 in an array that preferably surrounds axis 27 in a generally symmetrical pattern. An annular array of threaded bores is usually sufficient. One or more annular arrays of threaded bores may be used, and patterns other than annular arrays may be employed, if desired. Where test loads in excess of, for example, 300,000 pounds are to be applied, it may be desirable to increase the number of threaded bores by employing two or more generally concentric annular arrays of threaded bores, or the like. This increases the number of threaded jack bolts, which reduces the amount of torque that must be applied to each individual jack bolt. This keeps the amount of applied torque per jack bolt within the values that can be imposed by a single worker by hand. Embodiments of the present invention may thus be employed for generating extremely high tensile loads of, for example, 1,000,000 pounds or more without resorting to hydraulics or other expedients for generating such loads. The benefits of the present invention may thus be enjoyed for a range of test loads of from a few hundred to upwards of a million pounds or more.

A plurality of threaded jack bolts, of which 116 is typical, are adapted to being threadably received in threaded bores 114. The jack bolts 116 extend entirely through the flange element 112 and project towards the outer side of the adjacent frame element. The bearing ends of the jack bolts, of which 117 is typical, are positioned to bear generally against outer side 90. The bearing ends need not bear directly on outer side 90 so long as they are substantially rigidly supported, directly or indirectly, by the outer side of the first end. Typically, at least a load distributing member, for example, thrust collar element 108, is interposed between bearing ends 117 and outer side 90. In such an embodiment bearing ends 117 bear against the adjacent face, of which 106 is typical, of the thrust collar element. The opposed face of thrust collar element 108 bears generally although not necessarily directly against outer side 90. In the embodiment chosen for illustration, a load measuring assembly, in the form of a load cell 100 and an associated load distributing washer 94, is interposed between the opposed face of thrust collar element 108 and outer side 90. The load cell serves as a load measuring member. The opposed face of thrust collar element 108 bears directly against the adjacent face 104 of load cell 100, and the opposed face of load cell 100 bears directly against adjacent face 98 of load distributing washer 94.

In the embodiment chosen for purposes of illustration, the bearing ends 117 of the jack bolts thrust against a thrust receiving element, for example, thrust collar element 108, as they are tightened down. Annular axial openings 110 in element 108, 102 in load cell 100, and 96 in load distributing washer 94 are adapted to receiving the arbor element slidably therethrough. The element 108, load cell 100, and washer 94 are not supported by the arbor element. Thrust receiving element 108, load cell 100, and washer 94 are supported directly or indirectly by the outer side 90 of the first end. Tightening the jack bolts generally against the first end places all of the structure between the bearing ends 117 and outer side 90 in compression while at the same time placing the arbor element in tension.

A test load is applied by tightening jack bolts 116 in threaded bores 114. Preferably, the jack bolts are all torqued to approximately the same torque value so that the load is applied generally symmetrically around axis 27. Such tightening applies a tensile load to the arbor element along axis 27, which load is transmitted to the test specimen in the test zone 26. Because the arbor element is free to move relative to the first end, and the thrust receiving element 108 is generally supported by outer side 90 of the first end, the load that is applied by tightening the jack bolts 116 against element 108 places the test specimen in tension.

In those embodiments where the precise magnitude of the load applied in every test is to be measured, a load determining assembly is provided. Such a typical load determining assembly includes a load measuring member, for example, load cell 100, and a load indicating member, for example, digital read out member 118. The numeric magnitude of the test load can be determined, for example, by determining the amount of deflection that occurs in some part of the test setup when the test load is applied. Such deflection is conveniently measured, for example, by means of one or more strain gauges applied to an arbor element or incorporated in a load cell, or the like.

The load measuring member is preferably, but not necessarily, located along axis 27, and, depending on its placement, may measure under either compression or tension. A load measuring member in the form of a strain gauge attached, for example, to shank portion 36 of the arbor element would measure how much the arbor element stretches under the applied load. A load cell that measures in compression could, for example, be located between outer side 95 and washer 34. Load cells could be located, for example, in columns 16 and 18 and the readings summed to measure the applied load. A strain gauge applied directly to threaded mounting shaft 28 could serve as a load measuring member. As will be understood by those skilled in the art, other load measuring members and arrangements may be employed, if desired.

In the embodiment chosen for illustration, the opposed first and second ends of the frame assembly are generally defined respectively by a crosshead element 12, and a footing element 14. In the illustrated embodiment, two columns, 16 and 18, serve to maintain the crosshead and footing elements 12 and 14, respectively, spaced apart by a predetermined distance. In this embodiment, a rectangular frame defines a test zone 26 therewithin and provides a rigid support for the desired tensile strength test. The columns 16 and 18 are socketed in sockets 24 and 22, respectively, in a base plate member 20. As will be understood by those skilled in the art, other frame configurations may be employed, if desired. For example, a frame assembly wherein one or more of the elements of the frame assembly exhibits an arcuate geometry may be used, provided the frame is sufficiently rigid to permit accurate tests to be conducted.

For purposes of accommodating different test specimens and protocols it is desirable to provide for the adjustable mounting of at least one of the opposed first and second ends of the frame assembly. In the embodiment chosen for illustration, this adjustability is provided, for example by providing first end element 12 with guides 82 and 84. Guides 82 and 84 include cylindrical mounting bores 86 and 88. Pin bores 78 and 80 extend laterally across the bores 86 and 88, respectively. Mounting bores 86 and 88 are adapted to slidably receiving cylindrical columns 16 and 18 therethrough. Transverse bores, of which 70 and 72 are typical, are formed in the columns. Crosshead element 12 is adjustably mounted to columns 16 and 18 by inserting the columns into mounting bores 86 and 88 and sliding the columns to a position where pin bores 78 and 80 align with a set of the transverse bores in the columns. Pins 74 and 76 are then inserted through the mating pin and transverse bores to rigidly secure the first end 12 in the desired location on the columns. Second end 14 is likewise mounted to the columns 16 and 18 by way of pins 62 and 66 inserted through pin bores 64 and 68, respectively, and the mating transverse bores in columns 16 and 18. Column 16 is slidably received in mounting bore 54 in guide 56. Likewise, column 18 is slidably received in mounting bore 58 of guide 60. As will be understood by those skilled in the art, other systems may be used for adjusting the positions of the first and second ends relative to one another. Such other adjustment systems include, for example, threaded or ratchet adjustments, or the like.

For some purposes, an approximation of the test load is acceptable, and it is not necessary to determine the exact numeric value of the load applied in each test. In embodiments that are intended for such purposes, the approximate magnitude of the load can be determined by applying a predetermined amount of torque to tightening each of the jack screws 116 in the threaded bores 114. The total load applied by tightening each of the jack screws to a given torque value is approximately the same each time the jack screws are torqued down to that given value. A reasonable approximation of the total applied loads may be arrived at by calibrating the test setup. The magnitudes of the loads that result from the application of certain torque values are determined by such calibration. The application of the same torque values to the jack bolts will produce approximately the same loads in future tests.

The mounting of a test specimen in test zone 26 requires mounting fixtures that are adapted to the specific form of the test specimen. In the embodiment selected for purposes of illustration, a first specimen mounting fixture is mounted to the arbor element generally in the test zone 26. This fixture includes a block 44 that is mounted to shank portion 36 of the arbor element. Preferably, this mounting is effected by way of an axially extending threaded bore that mates with an external thread on the inner end of the arbor element. Block 44 is cut transversely to provide a transverse slot 46. Slot 46 is adapted to receiving a lifting loop 40 of a swiveling hoist ring therewithin. A pin 48 is inserted laterally through port 50 in block 44 from a direction generally normal to slot 46 and axis 27 at such a location that such insertion traps lifting loop 40 in slot 46. Nut 52 threadably engages the end of pin 48 and retains it in retaining association in block 44. Test specimens with other shapes would require different first specimen mounting fixtures.

A mounting fixture assembly is attached to the opposed end of the test specimen and to the second end of the frame assembly. The mounting fixture assembly includes a second specimen mounting fixture in the form of second block 42, a threaded mounting shaft 28, and an associated nut and washer, 32 and 34, respectively. In the embodiment chosen for illustration, the second mounting specimen must engage and hold a threaded stud 41. The second block 42 is preferably provided with an axially extending threaded bore that is adapted to threadably engage stud 41. Second block 42 is also preferably provided with an axially extending threaded bore that is adapted to threadably engaging shaft 28. Shaft 28 is rigidly anchored to footing element 14 by means of nut 32. The said first and second specimen mounting fixtures are adapted to holding said test specimen in a tensile strength testing configuration in test zone 26. The overall height of machine 10 is approximately 92 inches, and the base 20 is approximately 36 by 54 inches. In the illustrated embodiment, an axially extending gap 120 is provided to accommodate the stretching of the arbor element. Without gap 120 the block 44 would bear against inner side 91, which would invalidate the test, because the first end would be compressed generally between block 44 and the jack bolts.

An embodiment of the present invention that is suitable for applying test loads of from approximately 5,000 to 300,000 pounds has an arbor element that is approximately 25 inches long with a shank portion 36 that is approximately 15 inches long and approximately 2.5 inches in diameter, including an approximately 3.3 inch threaded end that is adapted to be threadably engaged with block 44. The threaded portion 38 is approximately 10 inches long and 4 inches in diameter.

The machine 10 is typically constructed of tool steel, however, any material or combination of materials, compatible with the functions and operation of a particular embodiment is contemplated as being within the scope of the present invention.

Test machine 10 has been described and shown with a hoist ring as the test specimen. As will be understood by those skilled in the art, a machine constructed according to the teachings of the present invention can be used with any test specimen of any configuration so long as suitable mounts can be crafted to safely mount the test specimen in the machine.

Many airframe components, for example, landing gear members, are proof tested. Critical structural elements in many different industries are proof tested. Such airframe components and structural elements, as well as many other test specimens can be tested using embodiments of the present invention.

Where machine 10 is intended for use as an engineering test machine in which test specimens are tested to destruction, special safety precautions must be taken. Shielding and guards must be provided so that broken pieces of the test specimen do not strike the operators or other machines or structures in the area when the test specimen breaks. Preferably, a damper is provided on the arbor so that the sudden breaking of the test specimen does not cause the arbor to suddenly jump uncontrollably through a distance until it impacts the frame. Such sudden unrestrained movement risks injury to the operator.

What have been described are preferred embodiments in which modifications and changes may be made without departing from the spirit and scope of the accompanying claims. It is therefore to be understood that, within the scope of the appended claims, the invention may be practiced otherwise than as specifically described.

What is claimed is:

1. A tensile strength testing machine comprising:
    a frame assembly including a crosshead element, a footing element, and at least two column elements engaged with and extending between said crosshead and footing elements and adapted to maintaining said crosshead and footing elements spaced from one another;
    an arbor assembly mounted to said crosshead element and including an arbor element extending axially slidably through said crosshead element from a first to a second side thereof, a first specimen mounting fixture attached to said arbor element on said first side, a thrust collar element mounted around said arbor element on said second side in a generally axially fixed position relative to said crosshead element, a load imposing flange element adapted to being mounted around said arbor element on said second side in a generally axially fixed location relative to said arbor element and having a plurality of threaded bores extending therethrough, a plurality of jack bolts threadably received in said threaded bores and adapted to bearing axially on said thrust collar element;
    a load measuring member measuringly associated with said arbor element;
    a load indicating member indicatingly associated with said load measuring member; and
    a mounting fixture assembly mounted to said footing element and including a second specimen mounting fixture, said first and second specimen mounting fixtures being adapted to securing a test specimen therebetween in a tensile strength testing configuration.

2. A tensile strength testing machine of claim 1 wherein said crosshead and footing elements are adjustably spaced from one another.

3. A tensile strength testing machine of claim 1 wherein said load measuring member comprises a load cell located on said second side.

4. A tensile strength testing machine of claim 1 wherein said load measuring member comprises a strain gauge measuringly associated with said arbor element.

5. A tensile strength testing machine comprising:
    a frame assembly including a crosshead element, a footing element, and at least two column elements engaged with and extending between said crosshead and footing elements and adapted to maintaining said crosshead and footing elements adjustably spaced from one another, said crosshead element having a first side generally opposed to said footing element, and a second side generally facing said footing element;

an arbor assembly mounted to said crosshead element and including an arbor element axially slidably mounted to said crosshead element, a first specimen mounting fixture attached to said arbor element on said second side, a thrust collar element mounted around said arbor element in a generally axially fixed position relative to said crosshead element on said first side, a load imposing flange element adapted to being mounted around said arbor element in a generally axially fixed location relative to said arbor element on said first side and having a plurality of threaded bores extending therethrough, and a plurality of jack bolts threadably received in said threaded bores and adapted to bearing axially on said thrust collar element; and a mounting fixture assembly mounted to said footing element and including a second specimen mounting fixture, said first and second specimen mounting fixtures being adapted to securing a test specimen therebetween in a tensile strength testing configuration.

6. A tensile strength testing machine of claim 5, including a load determining assembly adapted to determine a tensile load that has been applied to said test specimen.

7. Method of imposing a tensile load on a test specimen comprising:

providing a frame assembly including generally opposed first and second ends, an arbor assembly mounted to said first end, a mounting fixture assembly mounted to said second end, said arbor assembly and mounting fixture being adapted to holding a test specimen therebetween in tensioning configuration, said arbor assembly including an arbor element with a shank portion and a thrust receiving element mounted around said shank portion in a generally axially fixed position relative to said first end;

providing a load imposing flange element mounted around and in generally axially fixed position to said arbor element, said load imposing flange element including an array of threaded bores extending generally axially therethrough;

providing a plurality of jack bolts threadably received in said threaded bores and positioned to bear generally axially against said thrust receiving element;

mounting said test specimen in said tensioning configuration;

applying a tensile load to said test specimen by threadably tightening said jack bolts against said thrust receiving element; and determining when said tensile load has been applied to said test specimen.

8. Method of imposing a tensile load on a test specimen of claim 7 wherein said determining includes providing a load cell positioned to receive a compressive load that is generated by said threadably tightening.

9. Method of imposing a tensile load on a test specimen of claim 7 wherein said determining includes torquing said jack bolts to a predetermined value.

10. Method of imposing a tensile load on a test specimen of claim 7 wherein said determining includes providing a strain gauge measuringly associated with said shank portion.

11. Method of imposing a tensile load on a test specimen comprising:

selecting a said test specimen;

providing a frame assembly that defines a test zone and includes a frame member that has an outer side generally opposed to said test zone;

providing an arbor element that is mounted for generally axial movement relative to said outer side;

allowing said arbor element to project inwardly into said test zone and outwardly from said outer side of said frame member;

mounting said test specimen in said test zone including attaching said test specimen to said arbor element;

generally surrounding a portion of said arbor element that projects outwardly from said outer side with an array of jack bolts threadably mounted in a collar member that is axially fixed relative to said arbor element; and applying said tensile load to said specimen by tightening said jack bolts generally against said outer side.

12. A tensile strength testing machine comprising:

a frame assembly that defines a test zone and includes a frame member having an outer side generally opposed to said test zone;

an arbor element mounted for generally axial movement relative to said outer side, said arbor element projecting inwardly into said test zone and outwardly from said outer side and adapted to being attached to a test specimen mounted in said test zone; and a portion of said arbor element that projects outwardly from said outer side and being generally surrounded by an array of jack bolts threadably mounted in a collar member that is substantially axially fixed relative to said arbor element, said jack bolts being positioned to bear generally against said outer side.

* * * * *